United States Patent [19]

Albano et al.

[11] 4,341,737
[45] Jul. 27, 1982

[54] APPARATUS FOR CARRYING OUT CATALYTIC EXOTHERMIC AND ENDOTHERMIC HIGH-PRESSURE GAS REACTIONS

[75] Inventors: John V. Albano, Oradell; George Friedman, Clark, both of N.J.

[73] Assignee: The Lummus Company, Bloomfield, N.J.

[21] Appl. No.: 41,378

[22] Filed: May 22, 1979

[51] Int. Cl.³ .......................... B01J 8/04; C01C 1/04
[52] U.S. Cl. .................................. 422/148; 165/125; 422/191; 422/192; 422/195; 422/203
[58] Field of Search ............... 422/148, 191, 192, 193, 422/195, 203; 165/125

[56] References Cited

U.S. PATENT DOCUMENTS

| | | | |
|---|---|---|---|
| 3,302,705 | 2/1967 | Wilten, Jr. ............................ | 165/125 |
| 3,556,738 | 1/1971 | Scholer ................................ | 422/148 |
| 3,866,668 | 2/1975 | Doerner ............................ | 165/125 X |
| 4,101,281 | 7/1978 | Pagani .................................. | 422/148 |
| 4,152,407 | 5/1979 | Fuchs ............................... | 422/148 X |
| 4,230,669 | 10/1980 | Eagle et al. ........................... | 422/148 |

FOREIGN PATENT DOCUMENTS

| | | | |
|---|---|---|---|
| 1914246 | 9/1970 | Fed. Rep. of Germany ...... | 422/148 |
| 1940980 | 2/1971 | Fed. Rep. of Germany ...... | 422/148 |
| 1940478 | 4/1971 | Fed. Rep. of Germany ...... | 422/148 |

*Primary Examiner*—Michael S. Marcus
*Attorney, Agent, or Firm*—James N. Blauvelt

[57] ABSTRACT

Apparatus for carrying out catalytic exothermic and endothermic high-pressure gas reactions, comprising a single-walled pressure vessel or shell containing cross-flow (e.g., radial flow) heat transfer exchangers, a continuous catalytic bed having at least two stages, and means for effecting "cross-over" material flows from "outside" to "inside" (for exothermic reactions) and vice versa (for endothermic reactions), whereby conditions of: maximum gas temperature always being in the core of the apparatus, minimal pressure drop, and minimal compression of catalyst particles are achieved, along with significant economic savings in cost of the apparatus and catalyst (through extension of catalyst life).

6 Claims, 11 Drawing Figures

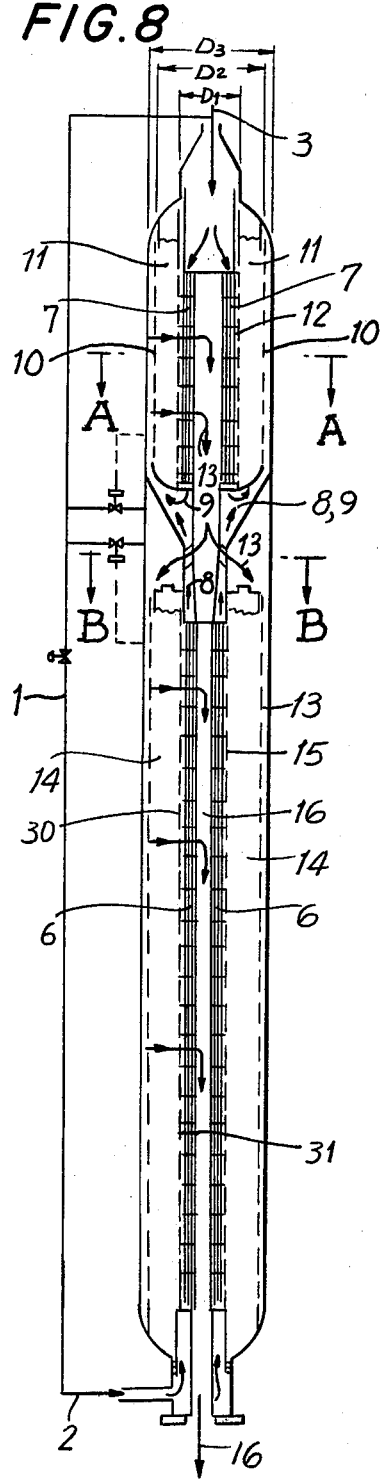
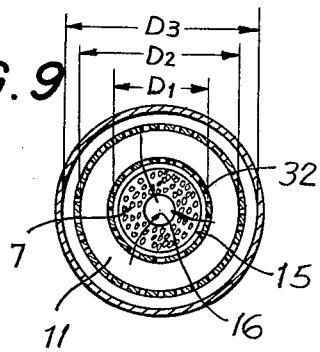
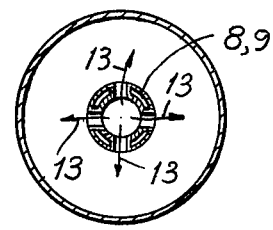
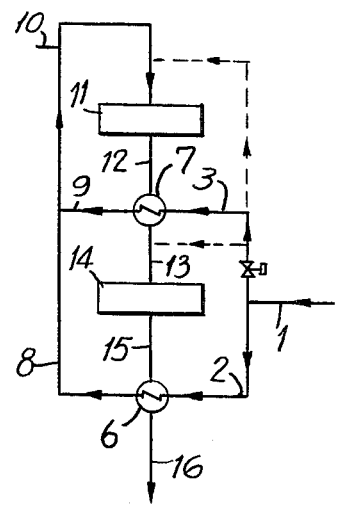

APPARATUS FOR CARRYING OUT CATALYTIC EXOTHERMIC AND ENDOTHERMIC HIGH-PRESSURE GAS REACTIONS

BACKGROUND OF THE INVENTION

1. Field of the Invention

This invention relates to an improved high-pressure catalytic apparatus for effecting exothermic or endothermic gaseous reactions therein such that maximum gas temperatures are always in the core of the apparatus and minimum pressure drop conditions and significant economies can be achieved, resulting in extension of catalyst life and a marked decrease in the capital cost of such apparatus.

More specifically, this invention relates to an improved high-pressure catalytic apparatus, capable of effecting either exothermic or endothermic gaseous reactions therein with the foregoing results, comprising a single-walled pressure vessel or shell containing cross-flow, as, e.g., radial flow, heat transfer exchangers, a continuous particulate catalyst bed having at least two stages, and means for effecting "cross-over" material flows such that, for exothermic reactions, material flows are radially directed inwardly from "outside" to "inside," whereas, for endothermic reactions, material flows are radially directed outwardly from "inside" to "outside."

2. Description of the Prior Art

Heretofore, the art has been replete with high-pressure catalytic reactors or converters for effecting the gaseous syntheses of such valuable materials as ammonia, methanol, hydrocyanic acid, hydrogen, methane, and styrene. Typically, such apparatus have had to be built to withstand the extreme pressures and temperatures associated with such syntheses, approximating wide limits varying, for example, from between about 1200 to 10,000 p.s.i.g. Thus, in order to accommodate the commercial production rates required, e.g., catalytic converters capable of generating 1000 tons of ammonia per day, double-walled reactor vessels of enormous size have had to be employed as shown in U.S. Pat. No. 3,567,404. However, the costs and difficulties of manufacturing such converters have likewise been enormous. Moreover, equipment sizing problems have also been encountered, since in order to maintain space and linear velocity conditions at reasonable pressure drops, converters of prohibitively large diameters, in view of their high operating pressures, are required. Furthermore, it is well known in the art that, for a given operating pressure and temperature, the larger the diameter of the vessel, the thicker its walls have to be. Since the materials of vessel construction are also influenced by the temperature as well as by the hydrogen partial pressure, the reason for use of conventional double-walled vessels in the past has been manifest.

Accordingly, the art has long been concerned with providing reactors or converters of increased production, suitable for large-scale reactions, within the limits of acceptable design criteria and having flow patterns of reactants which lend themselves to increased production through increased length of the reactor or converter rather than through an increase in such reactor's or converter's diameter.

This too has posed problems in view of the fact that, in order to accommodate the increased production requirements, tall reactors or converters on the order of 40–50 feet high are required. Since within such reactors or converters one or more beds of catalytic contact material have to be vertically disposed, maintenance of optimum space and linear velocity conditions without prohibitive pressure drops has not been attainable, and various means have been sought to solve this problem.

One such solution has been proposed in U.S. Pat. No. 3,567,404, which utilizes the conventional double-walled reactor, whereby the reactant gases are permitted to flow in a direction perpendicular to the longitudinal axis of the outer shell and the inner reaction zone, and across one or more catalyst beds in series, such that the gases flow from one bed to the next consecutive bed through a passageway therebetween, the direction of flow of the gases through said passageway being generally opposite to their direction of flow through the catalyst bed. The arrangement of flow in this manner greatly facilitates the manner in which the reaction is conducted and permits wide alteration of desirable variables. For example, by having reactant flow downward across one bed and upward through an adjacent bed, this flow pattern has the effect of shortening the converter by eliminating the passageways between the beds. However, such flow methods and patterns have been unsuccessful because they have been unable to satisfy the temperature requirements associated with optimal yields and maximum suppression of competing side reactions, notwithstanding the use of heat exchange means disposed to accommodate such flow methods and patterns. Moreover, these flow patterns are subject to increased flow resistance, thereby leading to increased pressure drops, and a considerably reduced circulation rate through the reactor for a given catalyst volume. The solution to this type of flow problem has been the adoption of radial flow means such as taught by (1) U.S. Pat. No. 3,372,988, which originated the idea of "means for passing a synthesis gas through the catalyst bodies successively in opposite radial directions;" and by (2) an improved version of radial flow in U.S. Pat. No. 3,472,631 whereby the reactant gases are made to flow through each successive catalyst bed layer more or less horizontally in the reverse direction to the preceding catalyst layer and around heat exchange tubes at turning points countercurrent to the fresh reactant gases.

Additionally, the concept of circulating feed gas through tubes disposed in the catalyst bed for cooling purposes, prior to actual contact of the feed gas with the catalyst, has been shown in U.S. Pat. Nos. 2,853,371; 3,041,161; 3,050,377; and 3,212,862. The alternative approach to this mode of cooling has been through the use of quench cooling and quench-type converters as shown in U.S. Pat. Nos. 2,495,262; 2,632,692; 2,646,391; 3,366,461; 3,396,685; 3,433,600; 3,443,910; 3,458,289; 3,475,136; 3,475,137; 3,498,752; and 3,663,179. In the prior art quench-type converters, the quench fluid has generally been added to the main reactant stream between separate beds consisting of solid catalyst granules, spheres, or the like. The quench-cooled apparatus, however, have suffered from the disadvantages of high pressure drop and increased cost and complexity.

Heretofore, however, none of the prior art high-pressure, catalytic apparatus for performing reactions in the gaseous phase have been effective for both exothermic and endothermic reactions; none have been single-walled apparatus adapted to accommodate radial material flow patterns integrated with cross-flow heat exchangers; and none of such apparatus have been successful at maintaining maximum gas temperatures in the core of the apparatus with minimum pressure drop conditions within the limits of acceptable design criteria and acceptable flow patterns of reactions. In particular, and most notable is the fact that the prior art has been unaware of the use of cross-flow, e.g., radial, heat exchangers (let alone of their use with single shell reactors), thereby to enable flow direction to be arranged to make gas expansion or contraction consistent with catalyst cross-section expansion or contraction. The present invention has been developed to fill this void, and it does so through means of a new conceptually-based design of apparatus which enables the use of a single-walled reactor or reactor system having multiple reaction stages, whereby a radial flow of reactants is developed in accordance with a "cross-over" pattern such that material flows are directed from "outside" to "inside" for exothermic reactions and vice versa for endothermic reactions. For exothermic reactions, the present apparatus provides one cross-flow heat transfer stage for each reaction stage. However, for endothermic reactions, the first heat transfer stage is external to the system (for example, it can be situated outside the reactor), and hence, for endothermic reactions, there are one fewer heat transfer stages than reactor stages.

SUMMARY OF THE INVENTION

In accordance with the present invention, there is provided a high-pressure apparatus for carrying out either catalytic exothermic or endothermic reactions in the gaseous phase, comprising a single or single-walled pressure containment vessel or shell for conducting such reactions therein in multiple stages, such pressure vessel or shell containing one or more cross-flow (e.g., radial flow) heat transfer exchangers and a continuous catalyst bed having a plurality of stages (at least two), with a cross-flow heat transfer stage after each reaction stage for exothermic reactions and one less cross-flow heat transfer stage than there are reaction stages for endothermic reactions, the arrangement of these stages being such as to provide "cross-over" material flows in a continuous, unidirectional flow path through the various catalyst and heat exchanger stages, such uni-directional flow path being from "outside" to "inside" for exothermic reactions and vice versa for endothermic reactions, thereby effectively maintaining the highest gaseous temperature in the core of the apparatus rather than on the exterior or pressure containment walls thereof and also minimizing pressure drop.

DESCRIPTION OF THE DRAWINGS

FIG. 8 depicts a simplified cross-sectional elevation of a two-stage converter useful, in accordance with the present invention, for ammonia synthesis.

FIG. 9 is a cross-sectional plan view of the ammonia converter shown in FIG. 8 taken along the lines A—A thereof.

FIG. 10 is a cross-sectional plan view of the interstage cross-over structure of the ammonia converter shown in FIG. 8 taken along the lines B—B thereof. And finally, FIG. 11 is a schematic flow-diagram, the temperature profile of which is discussed below, of a typical ammonia synthesis conducted in the present catalytic reactor or converter.

DESCRIPTION OF THE DRAWINGS AND PREFERRED EMBODIMENTS

Figure 2:
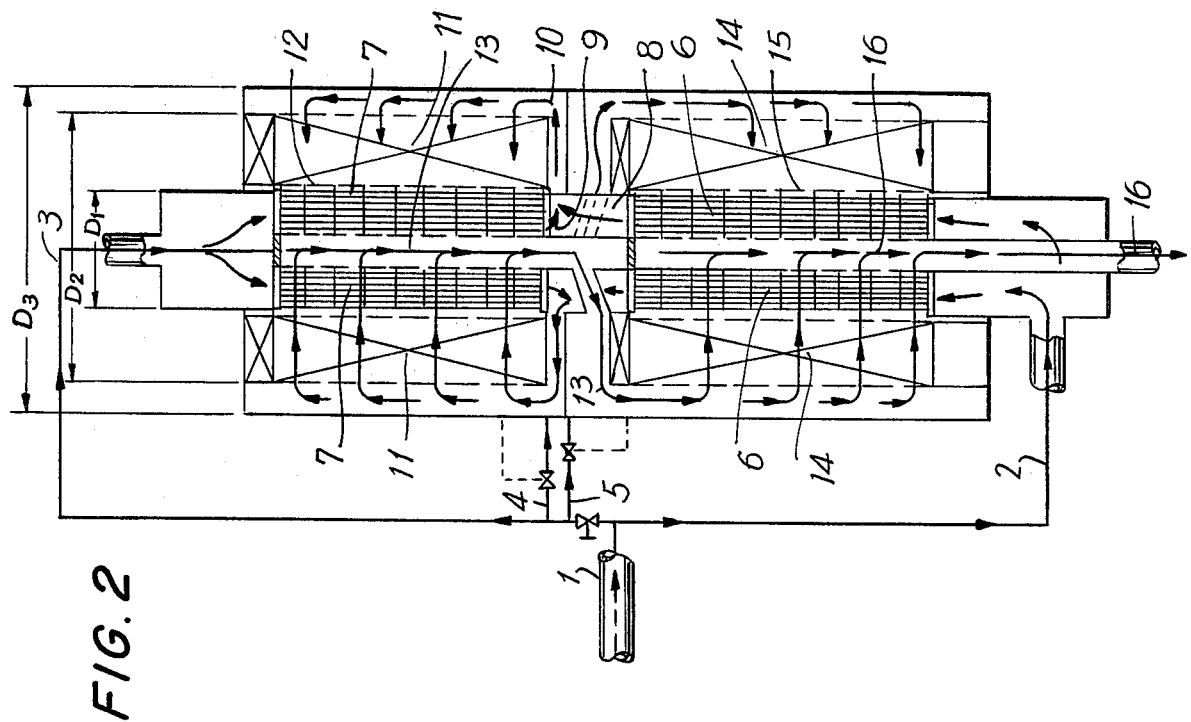
FIG. 2 shows a cross-sectional elevation of the present high-pressure apparatus, wherein the continuous particulate catalyst bed is depicted in the form of stacked stages, and the various inflow feed, and unreacted reactant/reaction effluent, flows are also shown.
Figure 1:
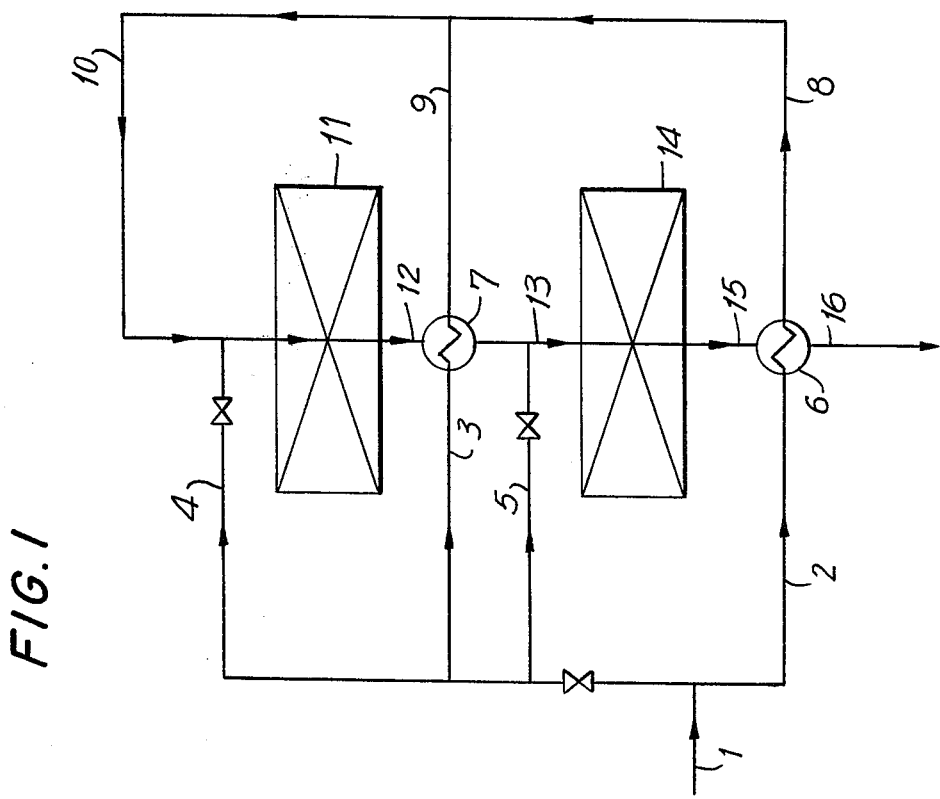
FIG. 1 shows a block-flow schematic diagram, illustrative of the inflow pattern of a typical two-stage, exothermic reaction system such as would be useful in the synthesis of ammonia, methanol, and methane.
Figure 3:
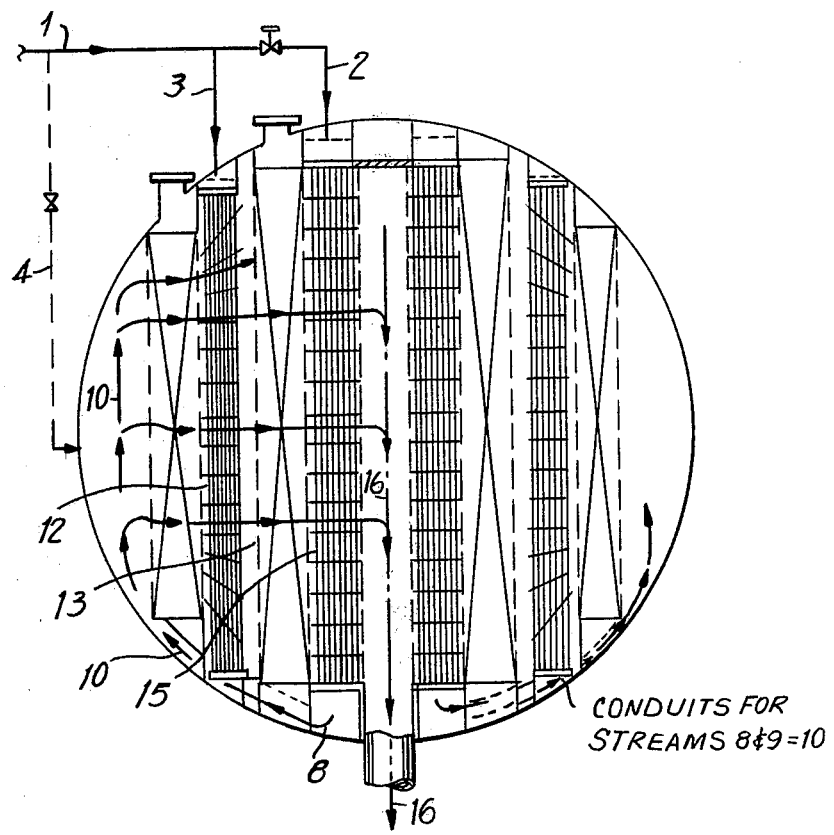
FIG. 3 depicts an alternative embodiment to that depicted in FIG. 2 and shows a cross-sectional elevation of the present high-pressure apparatus wherein the continuous particulate catalyst bed is depicted in the form of concentric stages, and the various inflow feed, and unreacted reactant/reaction effluent, flows are also shown.
Figure 4:
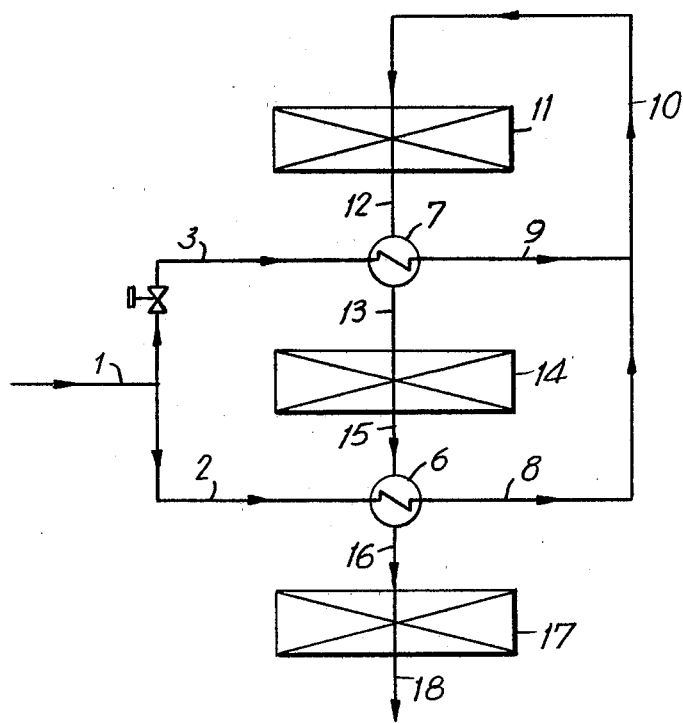
FIGS. 4 and 5 depict the outflow flow patterns of a typical three-stage endothermic outflow system, with FIG. 4 showing a block-flow diagram thereof and FIG. 5 showing a cross-sectional elevation of the present high-pressure apparatus wherein the particulate catalyst bed (represented in the form of stacked stages) and the various outflow unreacted reactant/reaction effluent outflows are also shown. For both endothermic systems, there is one less heat transfer stage than there are reaction stages.
Figure 5:
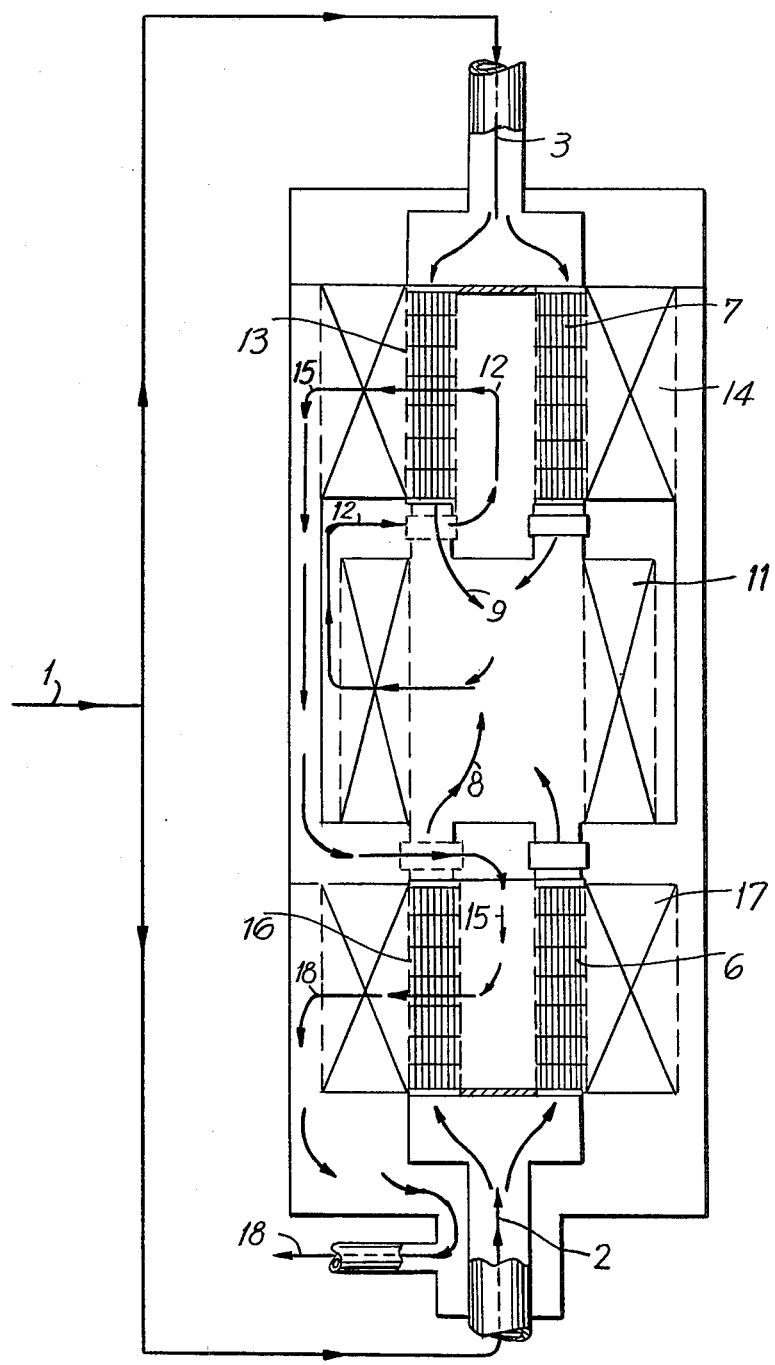
Figure 6:
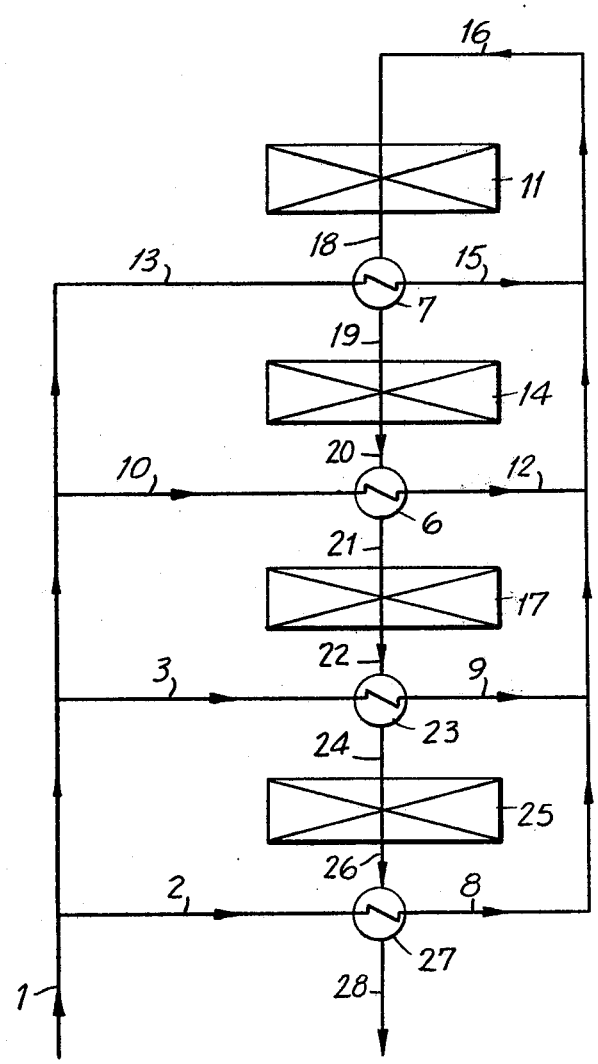
FIGS. 6 and 7 depict the outflow flow patterns of a typical four-stage exothermic flow system, with FIG. 6 showing a block-flow diagram thereof and FIG. 7 showing a cross-sectional elevation of the present high-pressure apparatus wherein the particulate catalyst bed is depicted in the form of either stacked or concentric stages, and the various outflow unreacted reactant-/reaction effluent outflows are also shown.
Figure 7:
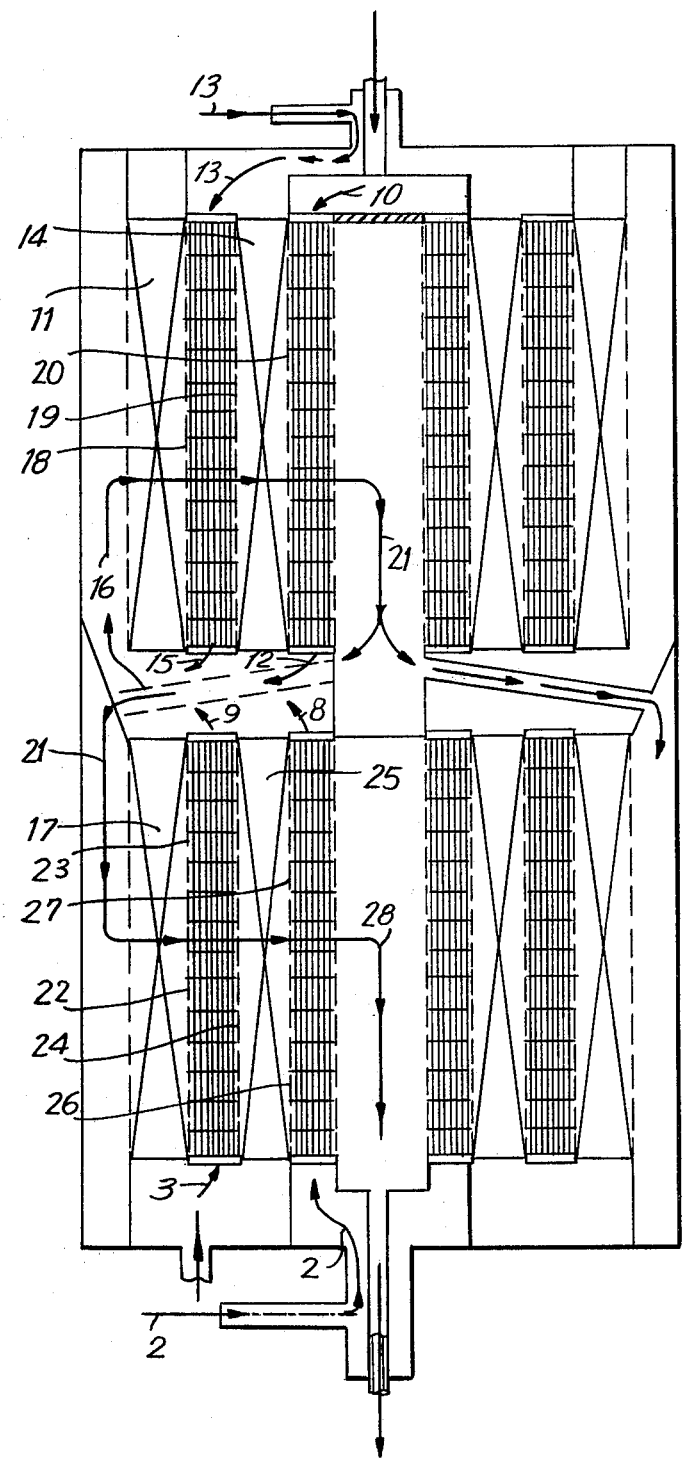

Referring now to FIGS. 1–3, a cold, fluid feed stream 1, which, in a preferred embodiment, would typically consist of an ammonia or methanol synthesis gas, is divided into a plurality of streams, of which two (2,3) are main feed streams and two (4,5) are by-pass streams. Main feed streams 2 and 3 are first passed, respectively, through the tube side of heat exchangers 6 and 7, where they become, respectively, heated streams 8 and 9 which are then joined into one main heated stream 10 which is passed into the first reaction stage 11 of a vertically oriented reactor or converter vessel and reacted under the required reaction conditions, which are well known in the art. From reactor first stage 11, an effluent stream 12 is passed through the shell side of heat exchanger 7 where its heat of reaction is exchanged with the cold main feed stream 3.

The cooled effluent 13 is introduced into the second stage 14 of the reactor, further reacted, and the resultant effluent therefrom 15 is passed through the shell side of the heat exchanger 6, where the heat of reaction effluent 15 is exchanged with the cold main feed stream 2. The resultant cooled effluent stream 16 is discharged from the reactor for downstream processing.

It is to be noted, with reference to FIGS. 1–3, that (1) flow direction is radially inward, thereby forcing the coolest gases within this exothermic system outward and that (2) temperature control is achieved by passing the cold fluid feed streams 1, 2, or 3 into streams 10 and 13.

The uni-directional flow patterns schematically depicted in FIG. 1 can perhaps better be visualized by recourse to FIGS. 2 and 3, which trace the course of a cold feed fluid stream to and from the two reactor stages and via the heat exchangers.

Similarly, by recourse to FIGS. 4-7, the uni-directional radial flow patterns of the fluid feedstream inflows and effluent inflows and outflows through the various reactor and/or heat exchanger stages can be seen with reference to other embodiments within the purview of the present invention such as, e.g., the use of concentric stages, a three-stage endothermic system (with particular emphasis on outflows); a four-stage exothermic system, etc. wherein the first two stages are as previously described with reference to FIGS. 1-3 and the third and fourth stages of the reactor are denoted 17 and 25; the various reactor effluent streams are denoted 18, 20, 22, and 26; the various heat exchanged (cooled) reactor effluent streams are denoted 19, 21, 24, and 28; and the third-stage, and fourth-stage, heat exchangers are denoted respectively as 23 and 27.

Referring now to FIG. 8, there is shown a preferred embodiment of the present invention, which depicts a two-stage ammonia synthesis converter. The process flows are as previously described with reference to FIGS. 1-7, particularly FIGS. 1-3.

A cold fluid feed stream 1, typically ammonia synthesis gas, is divided into a plurality of streams comprising two main feed streams 2 and 3, each of which is passed through a low pressure differential diffuser and then through the tube side of cross-flow heat exchangers 6 and 7, where they become, respectively, heated streams 8 and 9 which are then joined into one main heated stream 10 which is passed into the first stage 11 (comprising a bed of a conventional, active, particulate catalyst) of a vertically oriented reactor or converter vessel and reacted under the required, conventional reaction conditions. From the reactor first stage 11, an effluent stream 12 is passed through the shell side of heat exchanger 7 where its heat of reaction is exchanged with the cold main feed stream 3.

The cooled effluent 13 is introduced into the second stage 14 of the reactor, further reacted, and the resultant effluent therefrom 15 is passed through the shell side of the heat exchanger 6, where the heat of reaction of effluent 15 is exchanged with the cold main feed stream 2. The resultant cooled effluent stream 16 is discharged from the reactor for downstream processing.

Preferably, the reaction stages include perforated plates and screens 30 to facilitate catalyst retention as well as passage of gaseous reactant and product flows into and through the catalyst beds. Furthermore, it is also preferred that the annular catalyst containers 31 be perforated so as to minimize pressure differentials and eliminate flow gradiants.

Referring to FIG. 9, this shows a plan view of the interior of the reactor, specifically depicting the cross-flow exchanger 7, the active catalyst bed of the first reactor stage 11, the product effluent 15 of the second reaction stage, the final cooled product stream 16, and the catalyst retaining cylinders 32.

Referring to FIG. 10, this shows the heated reactant feed streams 8 and 9 for the first reaction stage and the exit patterns for inter-stage cross-over of the cooled product effluent 13 from said first reaction stage.

And, finally, referring to FIG. 11, this depicts a schematic flow diagram for a conventional two-stage, exothermic reaction system for ammonia synthesis, for which diagram a typical temperature profile of the various reactant or product flows is discussed below. For example, as shown in FIG. 11, the cold, fluid feed stream 1 is divided into two main streams 2 and 3. Feed streams 1, 2, and 3 are at a temperature of about 350° F. The flow of the other part 3 of feed stream 1, controlled by a valve, after passage through heat exchanger 7, attains a temperature of about 750° F. and is denoted as stream 9. Streams 8 and 9, both at about 750° F., unite into combined stream 10 which is at a temperature of about 750° F. and in fed into an active catalyst bed 11. The effluent 12 from the bed is at a temperature of about 954° F. Effluent 12, after being passed through heat exchanger 7, emerges as stream 13 at a temperature of about 735° F. and proceeds into the next reaction stage, active catalyst bed 14, from which the effluent 15 emerges at a temperature of about 885° F.

A temperature profile, such as is discussed above for FIG. 11 that would be typical for a 1500 MTD ammonia converter, such as shown in FIG. 8, is given in the Table 1 below, along with stream flow rates (defined according to the standard ACFS classification). The streams are numerically set forth in Table 1, as represented in FIG. 8.

TABLE 1

| Stream Number | Temperature, °F. | Flow Rate (ACFS) |
|---|---|---|
| 1 | 350 | 46.5 |
| 2 | 350 | 20.8 |
| 3 | 350 | 25.7 |
| 8 | 750 | 31.2 |
| 9 | 750 | 38.6 |
| 10 | 750 | 69.8 |
| 12 | 954 | 75.5 |
| 13 | 735 | 63.8 |
| 15 | 885 | 67.1 |
| 16 | 703 | 58.4 |

In many high-pressure catalytic converters or reactors, and in all ammonia and methanol designs thereof, there is a pressure containment problem which, under conventional conditions, becomes aggravated by changes in flow direction which increase the amount of pressure drop. A large part of the pressure containment problem arises from the fact that the usual feedstocks enter the reactor relatively cool and exit from it in a relatively hot state. For example, in the ordinary ammonia synthesis, the synthesis feed is introduced into the reactor at relatively cool temperatures approximating 750° F., and the product effluent exits therefrom at a relatively hot temperature of 950° F. With the present invention, the outer or pressure containment walls need only to be the thickness of a single wall because, through the use of uni-directional material flow patterns and the use of a system of cross-flow (e.g., radial flow) heat exchangers integrated with the corresponding system of reaction stages to promote such flow patterns, the coolest and lowest possible temperatures in the reactor are at the outer or pressure containment wall.

In common industrial practice, the number of reaction stages reaches an economic optimum very rapidly, e.g., in about two or three stages, owing to limitations in catalyst activity, the build-up of pressure drop, and the consequent increase in horsepower for the bulk transport of the gases flowing through such a system. And further complications are introduced in achieving optimal flow and temperature control throughout the system as the number of stages increases.

Application of the present apparatus to these practical problems enables the operator to realize increased yields, increased conversions, increased thermal efficiency, and decreased pressure drop.

In the most preferred or best mode embodiment of the present invention, "cross-flow" tubular heat exchangers are integrated with catalyst-containing annuli such that the shell-side fluid in the heat exchanger flows radially in a direction substantially normal to that in which the reactant fluid flows. However, the geometry of the arrangement between the radial flow heat exchangers and the catalyst-containing annuli is such that the respective cooling fluid of the heat exchangers and the fluid comprising the mixture of unreacted feedstock and product effluent in the catalyst tubes both follow a continuous uni-directional path in inter-related patterns, whereby the product effluent of each reaction stage is cooled in a subsequent heat exchange stage.

It is especially preferred that, for each exothermic reaction stage, one annular particulate catalyst bed and one cross-flow heat exchanger be provided (one less cross-flow heat transfer stage, as previously noted, being required for endothermic reactions), and this arrangement is amenable to a variety of operable forms.

For example, the heat exchangers and reaction stages could be positioned side-by-side in stacked vertical formation, with the reaction stages located closer to the pressure containment wall. In such an embodiment, as shown in FIG. 2, relative to an exothermic system, a cool mainstream would be fed to the lower heat exchanger and heated to reaction temperature, then passed from "outside" in a plurality of radially flowing streams to "inside" through both the upper reaction and exchange stages and then from "outside" to "inside" through the lower reaction and exchange stages.

In most preferred embodiments of this invention, the reactants are dispersed radially through the various catalyst beds and radially through the heat exchangers, and the cooling fluid of the heat exchangers passes through the exchanger tubes essentially normal to the flow of the reactants.

The invention will now be further illustrated by reference to the following specific, but non-limiting, examples.

EXAMPLE 1

This example illustrates the influence on catalyst life that reactant material fluid flows have, and compares the container volume changes for an inflow design and outflow design under the conditions proposed for practice in accordance with the present invention relative to synthesis of ammonia by the Haber process, operated at about 950° F. with a cold feed at about 750° F.; at reaction pressures of about 3000 psi, and a partial pressure of hydrogen of about 2300 psi; and a typical volumetric expansion (molal and thermal) of about 5–8 percent.

As shown in FIGS. 2, 8, and 9, relative to Example 1, the inner diameter of the heat exchange shell is $D_1$ and approximates 35"; the inner diameter of the catalyst annulus is $D_2$ and approximates 80"; and the inner diameter of the reactor itself is $D_3$ and approximates 90".

In an annular bed of catalyst under conditions of radial flow (with radial flow heat exchanger), the catalyst container volume expands more rapidly than the bulk catalyst as the temperature of the system is raised. For a given thermal cycle, i.e., the time from which the catalyst is loaded into the catalyst container at atmospheric temperature, the reactor is operated at reaction conditions (whereby the container volume increases relative to that of the catalyst and the catalyst physically settles), and the system is cooled to ambient temperature (whereby the container contracts and compresses the bulk catalyst, thereby crushing some catalyst particles and causing some degree of catalyst attrition), the computation of the container volume change—assuming an ambient temperature of 80° F. and $D_1$ being stainless steel Type 304 for inflow design and ferritic steel ($2\frac{1}{4}$ Cr—1 Mo) for outflow design; $D_2$ being ferritic steel ($2\frac{1}{4}$ Cr—1 Mo) for outflow design and stainless steel Type 304 for inflow design; and the respective coefficients of thermal expansion for Type 304 being $10.2 \times 10^{-6}$ in/in/°F. and for $2\frac{1}{4}$ Cr—1 Mo being $7.5 \times 10^{-6}$ in/in/°F.—can be calculated as follows:

$$V(\text{ambient}) = \frac{\pi}{(4)(144)} (80^2 - 35^2) = 28.225 \text{ ft}^3/\text{ft}$$

| Inflow Design | Outflow Design |
|---|---|
| $D_1 = (950-80) \times 10.2 \times 10^{-6} \times 35 = 0.311''$ | $(750-80) \times 7.5 \times 10^{-6} \times 35 = 0.176''$ |
| $D_2 = (750-80) \times 7.5 \times 10^{-6} \times 80 = 0.402''$ | $(950-80) \times 10.2 \times 10^{-6} \times 80 = 0.710''$ |
| $V(\text{hot}) = \frac{\pi}{4 \times 144} \times (80.402^2 - 35.311^2) =$ | $\frac{\pi}{4 \times 144} \times (80.710^2 - 35.176^2) =$ |
| $28.458 \text{ ft}^3/\text{ft}$ | $28.780 \text{ ft}^3/\text{ft}$ |
| $\Delta V = 28.458 - 28.225 = 0.233 \text{ ft}^3 \% =$ | $28.780 - 28.225 = 0.555 \text{ ft}^3 = 1.966\%$ |
| $0.233/28.225 = 0.825\%$ | |

EXAMPLE 2

For purposes of this example, the conventional ammonia catalytic converter design would be taken as a model in which the catalyst would be placed in a separate container, usually denoted as a "basket," which would be mounted concentrically within a standard pressure vessel used for ammonia synthesis, and in which model the annulus between the two vessels would contain the cold feed gas, thereby providing the option for designing the pressure container to be useful in a non-critical temperature range.

For axial flow reactors, this option would not be available since the catalyst container would be exposed to the maximum gas temperature. However, this option would be available for radial flow reactors such as those of the present invention wherein the operator would have the option of having 750° F. at the catalyst container wall via an "inflow" design or 950° F. through use of an "outflow" design.

Under the conditions of Example 1, the following calculation demonstrates there to be about a 25 percent increase in containment cost for the outflow system relative to the inflow system even without consideration of the increased complexity attributable to the presence of the basket. This calculation is based on the conventional requirements of an ASME Section VIII, Division 2 design for a pressure container.

| Inflow Design (Gas Flow = 750° F.) | $D_2 = 80''$ |
| --- | --- |
|  | $D_3 = 90''$ |
| Wall | Thickness |
| Pressure Containment Wall (P = 3000 psi, T = 750° F.) (Ferritic Steel = 2¼ Cr:1 Mo-A387-CR22C62) | 6.75" |
| Wall B | 0.375"(min.) |
| Outflow Design (Gas Flow T = 950° F.; | $D_1 = 80''$) |
|  | $D_2 = 90''$ |
|  | $D_3 = 100''$ |
| Wall | Thickness |
| Pressure Containment Wall (P = 3030 psi, T = 350° F.) (carbon steel - A516-70) | 7.25" |
| Basket Wall (External pressure 30 psi, T = 950° F.) (stainless steel-Type 304) | 1.00" |
| Wall E | 0.375"(min.) |

Assuming present relative costs per pound as the following: Carbon Steel = 1.0

| | |
| --- | --- |
| 2¼ Cr-1 Mo = 1.5 | |
| Type 304 = 4.0 | |
| The cost of A = 7.5 × 6.75 × 1.5 = | 238.6 |
| The cost of B = 6.7 × 0.375 × 1.5 = | 11.8 |
| | 250.4 |
| The cost of C = 8.3 × 7.25 × 1.0 = | 189.0 |
| The cost of D = 7.5 × 1.00 × 4.0 = | 94.2 |
| The cost of E = 6.7 × 0.375 × 4.0 = | 31.6 |
| | 314.8 |
| The relative cost ratio = $\frac{314.8}{250.4}$ = 1.25 | |

From Example 2, it can readily be seen that the outflow design results in a 25 percent increase in containment costs for the outflow design over the inflow design, apart from consideration of the problems of complexity attributable to the presence of the catalyst basket. Within the context of costs, a double wall reactor vessel, i.e., a pressure vessel containing a reactor basket, has several other constraints which increase cost and mechanical difficulty. For example, it is often considered prudent to incorporate a full diameter closure for the pressure vessel in order to facilitate assembly of the basket or to provide means of achieving direct access for periodic inspections of the pressure vessel. Such a closure is quite costly and increasingly difficult to achieve as diameter increases.

Moreover, because of the significant differential thermal expansion between the pressure vessel and the basket, it is not practical to achieve side entry into the reactor; therefore, all connections for instruments and by-passes must enter through the top of the basket, and be piped into the required locations in the reactor. It is therefore manifest that neither of the above constraints exists for a single-walled vessel; for the access opening need only be large enough to accommodate passage of the heat exchanger tubular bundles; accordingly, side entry into the single-walled reactor is simple and direct.

As and wherever defined herein, the terminology "single" or "single-walled" pressure vessel or shell, or "single" or "single-walled" apparatus, reactor, or converter, or the thickness thereof is meant to denote the conventional meaning such terminology has in the art as, for example, defined in Section VIII Rules for Construction of Pressure Vessels, Division 2—Alternative Rules; relative to the ASME Boiler and Pressure Vessel Code, An American National Standard (ANSI/ASME BPV-VIII-2), 1977 Edition, July 1, 1977, of the American Society of Mechanical Engineers.

In like manner, the metals of construction of the apparatus of the present invention in respect of the exothermic or endothermic reaction conditions under which such apparatus is intended to operate, as defined herein, are conventionally determinable, as, e.g., from application of the so-called "Nelson Chart" of G. A. Nelson contained in "Steels for Hydrogen Service at Elevated Temperatures and Pressures in Petroleum Refineries and Petrochemical Plants" of the American Petroleum Institute, API Publication 941, Second Edition, June 1977.

As will be apparent, the essential basis of the present invention is predicated, as has been stated or suggested previously, upon achieving, to the greatest extent possible, conditions of minimal pressure drop and compression of catalyst particles, thereby leading to increased conversions, yields, catalyst life, and thermal efficiency, by means of the utilization and deployment of uni-directional process or effluent flow patterns and of a system of cross-flow, e.g., radial flow, heat exchangers integrated with the corresponding system of reaction stages to promote such flow patterns such that, for exothermic reactions, the uni-directional process or effluent flow proceeds inwardly from the pressure containment walls of the reactor and vice versa for endothermic reactions. As will also be apparent, the present invention provides the potential for achieving large production capacity within a single reactor without increasing engineering complexity and without requiring new art or techniques for welding or pressure vessel fabrication. Accordingly, such important parameters as nature and use or deployment of catalysts, reactants, etc. and general process conditions are, for purposes of this invention, conventional in nature, as will readily be apparent to those skilled in the art in view of the above description of the invention.

It will be obvious to those skilled in the art that many modifications may be made within the scope of the present invention without departing from the spirit thereof, and the invention includes all such modifications.

What is claimed is:

1. A reactor for performing catalytic reactions in the gaseous phase, consisting essentially of a single-walled pressure shell, containing means defining a plurality of spaced apart, in a radial direction, substantially concentrically disposed annular catalyst beds with particulate catalyst in each bed; a plurality of annular shaped, substantially concentrically disposed cross-flow heat exchange means; said annular catalyst beds and said annular heat exchange means being substantially concentric and alternatingly disposed: means for passing a synthesis fluid into said shell through said heat exchange means and said catalyst beds in a radial direction; each said cross-flow heat exchange means being operatively associated with each of said catalyst beds for providing inter-stage feed-effluent heat exchange and having a shell side and a tube side adjacent one end of said bed wherein the shell-side fluid in each said cross-heat exchange means flows in a radial direction and substantially normal to that in which the tube-side fluid flows; and means for withdrawing a product gas from the pressure shell.

2. A reactor according to claim 1, wherein said plurality of substantially concentric catalyst beds and corresponding heat exchange means are in a vertical stacked array of concentric stages, each array comprises at least two catalyst beds substantially concentrically disposed about one another.

3. A reactor according to claim 2, wherein said plurality of substantially concentric catalyst beds and corresponding heat exchange means are substantially concentrically disposed about one another.

4. A reactor according to claim 1, 2 or 3, wherein said annular cross-flow heat exchange means are closer to the pressure containment wall than said catalyst bed.

5. A reactor according to claim 1, wherein the reaction performed is endothermic whereby said shell side fluid is directed in a radially outward direction.

6. A reactor according to claim 1, wherein the reaction performed is exothermic whereby the shell side fluid is directed in a radially inward direction.

* * * * *